(12) United States Patent
Shekalim

(10) Patent No.: US 8,465,509 B2
(45) Date of Patent: Jun. 18, 2013

(54) APPARATUS AND METHOD FOR REMOVING DEPOSITS FROM TUBULAR STRUCTURE, PARTICULARLY ATHEROMA FROM BLOOD VESSELS

(76) Inventor: Avraham Shekalim, Nesher (IL)

( * ) Notice: Subject to any disclaimer, the term of this patent is extended or adjusted under 35 U.S.C. 154(b) by 951 days.

(21) Appl. No.: 11/885,158

(22) PCT Filed: Feb. 21, 2006

(86) PCT No.: PCT/IL2006/000219
§ 371 (c)(1),
(2), (4) Date: Aug. 27, 2007

(87) PCT Pub. No.: WO2006/090366
PCT Pub. Date: Aug. 31, 2006

(65) Prior Publication Data
US 2008/0147103 A1    Jun. 19, 2008

Related U.S. Application Data

(60) Provisional application No. 60/656,404, filed on Feb. 28, 2005.

(51) Int. Cl.
*A61B 17/22* (2006.01)
(52) U.S. Cl.
USPC .......................................................... 606/159
(58) Field of Classification Search
USPC .......... 604/96.01, 103.06; 606/159, 191–192, 606/194; 623/1.11–1.14
See application file for complete search history.

(56) References Cited

U.S. PATENT DOCUMENTS

| | | | |
|---|---|---|---|
| 5,209,749 A | | 5/1993 | Buelna |
| 5,370,653 A | * | 12/1994 | Cragg ............................ 606/170 |
| 5,405,378 A | * | 4/1995 | Strecker ....................... 623/1.12 |
| 5,616,149 A | | 4/1997 | Barath |
| 5,628,746 A | * | 5/1997 | Clayman .......................... 606/45 |
| 5,779,698 A | * | 7/1998 | Clayman et al. ................ 606/39 |
| 5,782,903 A | * | 7/1998 | Wiktor .......................... 623/1.22 |
| 5,904,679 A | * | 5/1999 | Clayman .......................... 606/39 |
| 6,315,792 B1 | * | 11/2001 | Armstrong et al. .......... 623/1.23 |
| 6,500,186 B2 | | 12/2002 | Lafontaine |
| 6,663,661 B2 | * | 12/2003 | Boneau ........................ 623/1.11 |
| 8,052,701 B1 | * | 11/2011 | Cox et al. ....................... 606/159 |
| 2003/0078606 A1 | * | 4/2003 | Lafontaine et al. ............ 606/159 |
| 2004/0122465 A1 | * | 6/2004 | McMurtry et al. ............ 606/194 |
| 2005/0021071 A1 | | 1/2005 | Konstantion et al. |
| 2006/0111736 A1 | * | 5/2006 | Kelley .......................... 606/159 |

* cited by examiner

*Primary Examiner* — Ryan Severson
*Assistant Examiner* — Ashley Fishback
(74) *Attorney, Agent, or Firm* — Mark M. Friedman

(57) ABSTRACT

Apparatus for removing deposits from a selected location on the inner surface of a tubular structure, includes an expansible device introducible into the tubular structure, and at least one scraper cord carried on the outer surface of the expansible device so as to engage the inner surface of the tubular structure upon the expansion of the expansible device, and to be movable therealong to scrape away the deposits from the inner surface of the tubular structure. Preferred embodiments are described in the form of a catheter for removing atheroma or other undesirable deposits from blood vessels, wherein the expansible device is an inflatable balloon, and a flushing device is provided to flush out the scraped away deposits. The catheter preferably includes a plurality of such scraper cords occupying different portions of the inflatable balloon or different layers thereon, and individually movable over the outer surface thereof to produce a controlled and gentle scraping action.

20 Claims, 5 Drawing Sheets

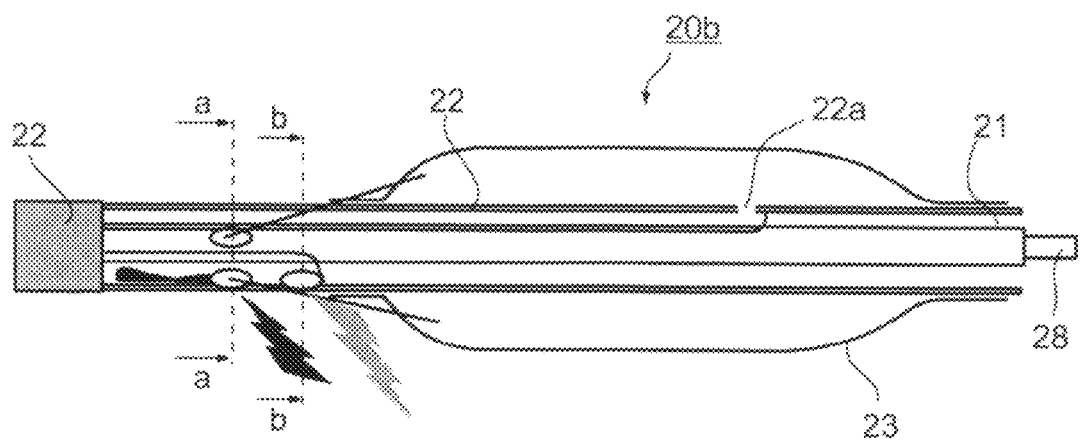
Fig. 7
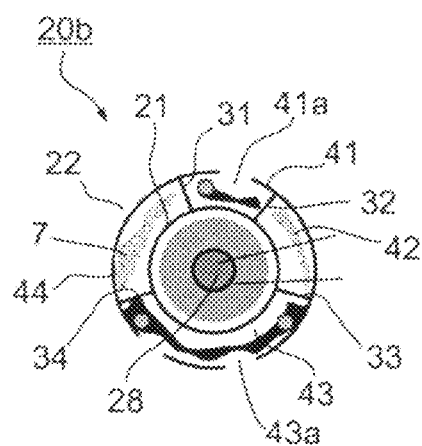 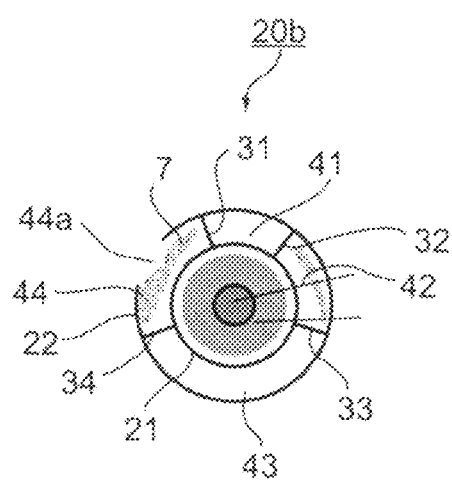
Fig. 8a  Fig. 8b

APPARATUS AND METHOD FOR REMOVING DEPOSITS FROM TUBULAR STRUCTURE, PARTICULARLY ATHEROMA FROM BLOOD VESSELS

RELATED APPLICATIONS

This Application is a National Phase of PCT Patent Application No. PCT/IL2006/000219 having International Filing Date of Feb. 21, 2006, which claims the benefit of U.S. Provisional Patent Application No. 60/656,404 filed on Feb. 28, 2005. The contents of the above Applications are all incorporated herein by reference.

FIELD AND BACKGROUND OF THE INVENTION

The present invention relates to apparatus and methods for removing deposits from tubular structures. The invention is particularly useful when implemented in a catheter for removing atheroma (e.g., deposits or degenerative accumulations) from blood vessels, and is therefore described below with respect to such catheters.

Fatty deposits accumulated in the coronary or peripheral arteries of a human patient seriously threaten the health of the patient. One method of treating this condition is bypass surgery in which a portion of the affected vessel is replaced by a section of a healthy vessel. Since this treatment involves open surgery, which inherently presents substantial risk to the patient, it is generally used only as a last resort where other treatments are not available.

Various percutaneous coronary intervention (PCI) treatments are currently available to open a narrowed or blocked segment of a blood vessel. One such treatment is balloon angioplasty, in which a balloon catheter is inserted into the body, manipulated to the location where the blockage appears to be, and inflated to expand the lumen and thereby to increase blood flow. A stent may be applied inside the blood vessel to provide support for the vessel in its expanded condition. However, an angioplasty treatment is frequently followed by a subsequent renarrowing of the blood vessel, requiring a repeat angioplasty treatment.

Another treatment in use is an atherectomy procedure, which involves the removal of the atheroma from the affected vessel with a cutting device delivered to the treatment site by a catheter. The known artherectomy treatments, however, are subject to a number of serious risks, including the possibility of a heart attack during the procedure, a closing of the artery necessitating emergency bypass surgery, bleeding caused by damage to the vessel walls, and irregular heart rhythms caused by the trauma to the body. In addition, an atherectomy treatment is very costly and also can lead to early complications.

Another treatment recently proposed is described in US Published Application 2005/0021071A1, published Jan. 27, 2005, in which a scoring structure, e.g. in the form of a separate expandable cage, is carried by an inflatable balloon so as to score the stenotic material when expanded by the balloon in the blood vessel. However, this proposed treatment would also appear to be subject to many of the foregoing risks and drawbacks.

OBJECTS AND BRIEF SUMMARY OF THE PRESENT INVENTION

One object of the present invention is to provide an apparatus and a method for removing deposits from tubular structures which apparatus and method have a number of advantages over the previously-mentioned techniques, as will be described more particularly below. Another object of the invention is to provide a catheter of a novel construction for removing atheroma and like deposits from blood vessels.

According to one aspect of the present invention, there is provided apparatus for removing deposits from a selected location on the inner surface of a tubular structure, comprising: an expansible device constructed such that in its non-expanded condition, it is introducible into the tubular structure, manipulatable therein to the selected location of the tubular structure, and radially-expansible therein to engage the inner surface of the tubular structure and the deposits to be removed; and at least one elongated, scraper cord carried on the outer surface of the expansible device, said scraper cord being of a flexibility and a thickness to engage the inner surface of the tubular structure upon the expansion of the expansible device, and having a circumferentially-extending intermediate length axially movable with respect to and along the outer surface of the expansible device in the expanded condition to scrape away the deposits from the inner surface of the tubular structure.

According to another aspect of the present invention, there is provided a method for removing deposits from a selected location on the inner surface of a tubular structure, comprising: introducing into the tubular structure an expansible device carrying on its outer surface at least one elongated, flexible scraper cord having an intermediate length extending circumferentially of said expansible device; manipulating the expansible device while in its non-expanded condition to the selected location of the tubular structure; radially expanding the expansible device to cause its outer surface, and the scraper cord carried thereon, to engage the inner surface of the tubular structure and the deposits thereon to be removed; moving the scraper cord along and between the outer surface of the expansible device and the inner surface of the tubular structure, to thereby scrape away the deposits therefrom; radially contracting the expansible device; and removing the expansible device from the tubular structure.

As indicated earlier, the apparatus and method of the present invention are particularly useful when implemented in a catheter for removing atheroma or other deposits on the inner surfaces of blood vessels.

Accordingly, and in accordance with a particular aspect of the present invention, there is provided a catheter for removing atheroma or other undesirable deposits from selected locations in blood vessels, comprising: an inflatable balloon constructed such that in its non-expanded condition, it is introducible into the blood vessel, manipulatable therein to the selected location of the blood vessel, and inflatable therein to engage the inner surface of the blood vessel and the deposits to be removed; and at least one elongated scraper cord carried on the outer surface of the inflatable balloon, said scraper cord being of a flexibility and a thickness to engage the inner surface of the blood vessel upon the expansion of the inflatable balloon, and having a circumferentially-extending intermediate length axially movable with respect to and along the outer surface of the balloon in its inflated condition to scrape away the deposits from the inner surface of the blood vessel.

The scraper cord or cords may be metal or plastic, of circular or non-circular (e.g., rectangular or square) cross-section, of a single strand or a plurality of strands twisted together, of a selected diameter (or thickness), and of a selected number and disposition over the inflatable balloon, all according to the particular condition of the patient being treated. Preferably, there are a plurality of such scraper cords carried on the outer surface of the inflatable balloon, occupying different portions thereof, and/or different layers thereon. The apparatus preferably further includes a flushing device for flushing out the deposits scraped away from the inner surface of the blood vessel.

The invention thus provides a new treatment for removing atheroma or other such deposits from blood vessels by using a scraper balloon catheter, or SBC. An SBC treatment for removing atheroma provides a number of advantages over the previous treatments used for this purpose. One important advantage is that an SBC treatment subjects the patient to substantially less shock and trauma, and substantially less danger of closing-off or damaging the treated blood vessel, thereby substantially reducing the health risks involved. In addition, an SBC treatment enables the catheter, particularly the number, layout, etc. of scraper cords thereon, to be more closely selected and controlled according to the condition of the particular patient. Further, SBC catheters produced in accordance with the present invention are much less costly, and can be more simply controlled, than catheters used in other atherectomy procedures.

Further features and advantages of the invention will be apparent from the description below.

BRIEF DESCRIPTION OF THE DRAWINGS

The invention is herein described, by way of example only, with reference to the accompanying drawings, wherein:

FIG. 7 more particularly illustrates the various passageways in the distal section of the catheter of FIG. 6; and FIGS. 8a and 8b are transverse sectional views along lines a-a and b-b of FIG. 7.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

As indicated earlier, the apparatus and method of the present invention are broadly useful for removing deposits from a selected location on the inner surface of various types of tubular structures both in the medical and non-medical fields. The method and apparatus of the invention, however, are particularly useful when implemented in a catheter, hereinafter called a scraper balloon catheter, or SBC, for removing atheroma and other deposits on the inner surface of blood vessels, and the invention is therefore described below particularly with respect to this application.

Figure 1A:
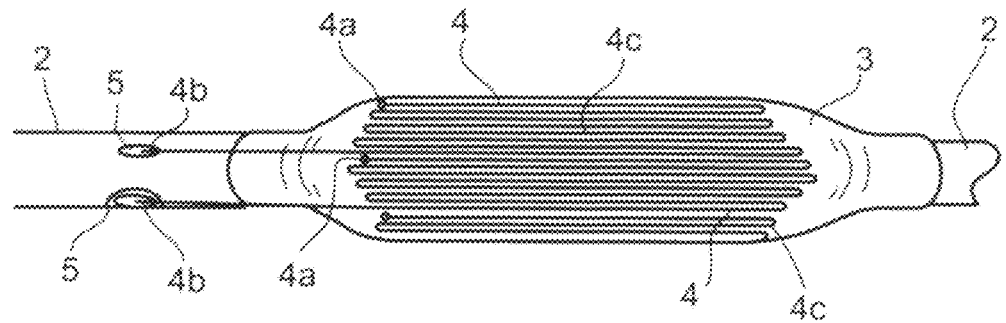
FIGS. 1a-1c illustrate the scraper-cords layout in one form of scraper balloon catheter (SBC) constructed in accordance with the present invention, and different stages in its use.
Figure 1B:
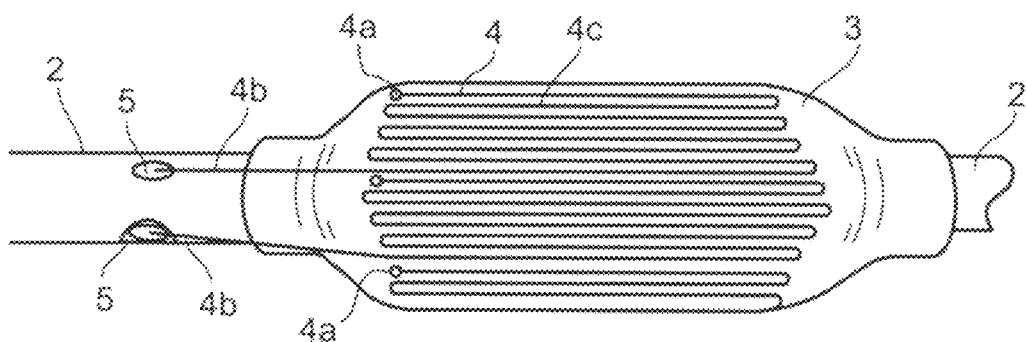
Figure 1C:
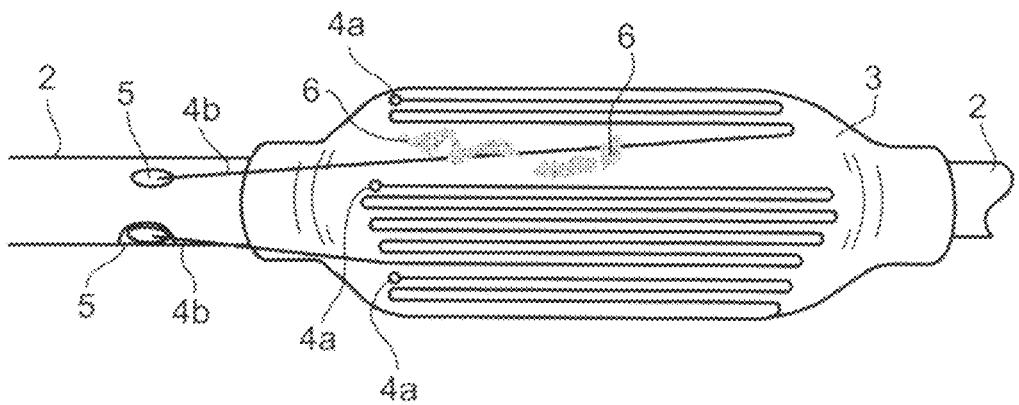

FIGS. 1a-1c illustrate the distal section of a scraper balloon catheter (SBC) constructed in accordance with the present invention, and particularly three stages in the use of the catheter in an atherectomy procedure for opening up a narrowed blood vessel to increase blood flow. The catheter illustrated in FIGS. 1a-1c includes an elongated flexible tube 2 of any known construction carrying a balloon 3 also of a known construction at the distal end of the tube. According to the present invention, at least one, and preferably a plurality as shown, flexible scraper cords 4 are carried on the outer surface of balloon 3 in a manner which permits the expansion of the balloon and which, when the balloon is expanded, permits the scraper cords 4 to engage, and to be moved with respect to and along, the outer surface of the balloon in its expanded condition to scrape away the atheroma or other deposits from the inner surface of the blood vessel in which the balloon catheter is introduced.

In the embodiment illustrated in FIGS. 1a-1c, there are plurality of flexible scraper cords 4 carried on the outer surface of inflatable balloon 3 to occupy substantially the complete outer surface of the balloon contacting the inner surface of the blood vessel when the balloon is inflated. As indicated earlier, each scraper cord 4 may be a single strand of metal or plastic of circular or other cross-section, or may be a plurality of such strands twisted together. Each cord 4 has a distal end 4a fixed to the outer surface of balloon 3, preferably to the proximal end of the balloon, and a proximal end 4b passing through an opening 5 in catheter tube 2 to permit the cord to be manipulated from the proximal end of the catheter, as will be described more particularly below. Each cord 4 further includes an intermediate portion 4c, between the two ends 4a, 4b, in a folded condition, defining a plurality of interconnected direction-alternating, or zigzag, sections extending generally longitudinally of the outer surface of balloon 3. Each scraper cord 4 is releasably retained on the outer surface of balloon 3 in the configuration illustrated in FIG. 1a, e.g. by a pressure-sensitive adhesive, but is movable, by a force applied to its proximal end 4b, along the outer surface of the balloon as the cord is pulled in the proximal direction (leftward in FIG. 1a) through its opening 5 in catheter tube 2.

FIG. 1a illustrates the non-expanded condition of balloon 3 as the catheter is introduced into the blood vessel to be treated. This catheter is manipulated to the location of the atheroma to be removed, at which time balloon 3 is inflated to cause its outer surface to engage the inner surface of the blood vessel. FIG. 1b illustrates the inflated condition of the balloon 3. Since the scraper cords 4 are in the illustrated folded condition, are flexible, and are releasably retained on the outer surface of balloon 3, they permit the inflation of the balloon. This causes the folds in the intermediate portion 4c of each scraper cord to spread apart in the circumferential direction to accommodate the increased diameter of the balloon.

FIG. 1c illustrates the condition wherein the proximal end 4b of a scraper cord 4 is being pulled in the proximal direction through its respective opening 5. This causes the intermediate portion 4c of the scraper cord to gradually unfold and to move along the outer surface of the balloon 3. Since the cord is firmly pressed by the balloon against the inner surface of the blood vessel, this movement of the cord causes it to scrape away portions of the atheroma, shown at 6 in FIG. 1c with which the scraper cord is in contact.

It will thus be seen that pulling each scraper cord 4 in the proximal direction (leftwardly in FIG. 1c) through the respective opening 5 will cause the respective cord to move along the outer surface of balloon 3 and to scrape away atheroma engaging the respective portion of the outer surface of balloon 3. By thus pulling out each cord, the surface of the blood vessel occupied by the cord in its folded condition is gently and gradually scraped away of any adhering atheroma. After the cord has thus been drawn out to scrape away its respective portion of the blood vessel, the next cord may then be drawn out to produce the same scraping action with respect to the surface of the blood vessel contacted by its folds. It will be appreciated, however, that two or more cords may be drawn out at the same time, if desired.

As shown in FIGS. 1a-1c, the distal end 4a of each scraper cord 4 is fixed to the outer surface of the balloon, preferably at the proximal end of the balloon. However, in some applications the distal end of the cord may also be releasably held to the balloon such that the complete scraper cord can be drawn through its respective opening 5 from the balloon.

Figure 2A:
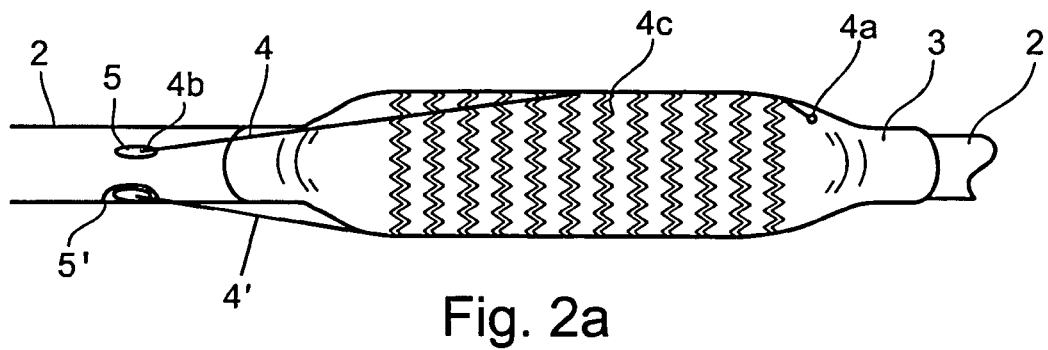
FIGS. 2a and 2b illustrate another formation of scraper cords on a balloon in the non-expanded and expanded conditions of the balloon.
Figure 2B:
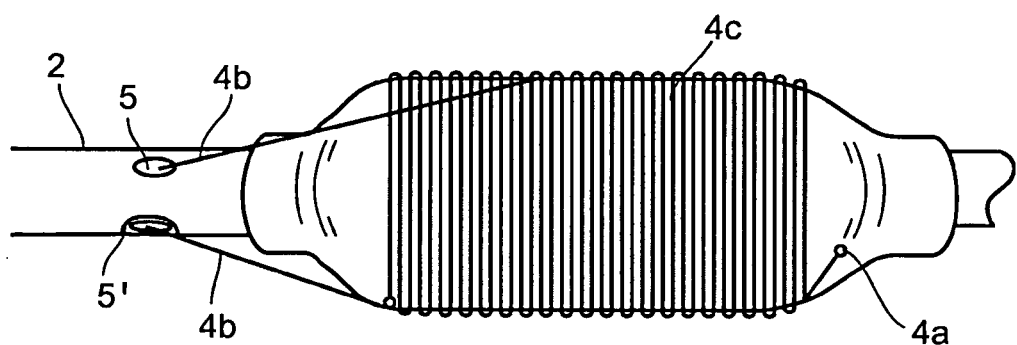

FIGS. 2a and 2b illustrate another disposition of the scraper cords on the outer surface of the balloon in the non-expanded and expanded condition of the balloon. Thus, each scraper cord 4 includes a distal end 4a firmly fixed to the outer face of the balloon 3, a proximal end 4b passing through an opening 5 in the catheter tube 2, and an intermediate portion 4c which is folded into a plurality of interconnected direction-reversing sections extending circumferentially of the balloon. FIG. 2a illustrates one scraper cord, in full lines at 4, covering one-half of the circumferential surface of balloon 3, and another scraper cord, in broken lines at 4', of a similar configuration covering the other (unseen) half of balloon 3 and passing through another hole 5' in the catheter tube 2. As further shown in FIG. 2a, each of the circumferentially-extending sections of the folded intermediate portion 4c of each scraper cord is of a zigzag configuration so as to permit expansion of balloon 3. It will thus be seen that the construction illustrated in FIG. 2a permits the balloon to be expanded as shown in FIG. 2b. It will also be seen that in the expanded condition of the balloon, pulling one cord 4 in the proximal direction (leftwardly, FIG. 2a) will cause the cord to be gradually released from the outer surface of balloon 3 and to move along the respective surface such as to scrape-away any atheroma engaged by the cord at the respective face of the balloon, whereas pulling the other cord 4' in the proximal direction will produce the same result with respect to the opposite face of the balloon.

Figure 3:
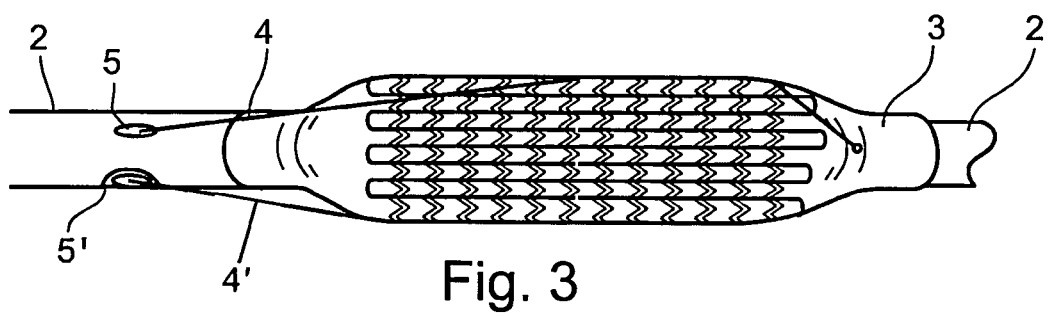
FIGS. 3 and 4 illustrate still other scraper cord formations in accordance with the present invention.

FIG. 3 illustrates a construction wherein the balloon 3 includes a plurality of scraper cords on its outer surface, but arranged in two layers, one layer including the longitudinally-extending sections shown in FIGS. 1a-1c, and the other layer including the circumferentially-extending sections of FIGS. 2a and 2b. In such a construction, the outer layer of scraper cords will first be peeled away as described above with respect to FIGS. 2a and 2b, and thereafter the inner layer of scraper cords will be peeled away as described above with respect to FIGS. 1a-1c, to thereby enable more complete removal of the atheroma from the blood vessel.

Figure 4:
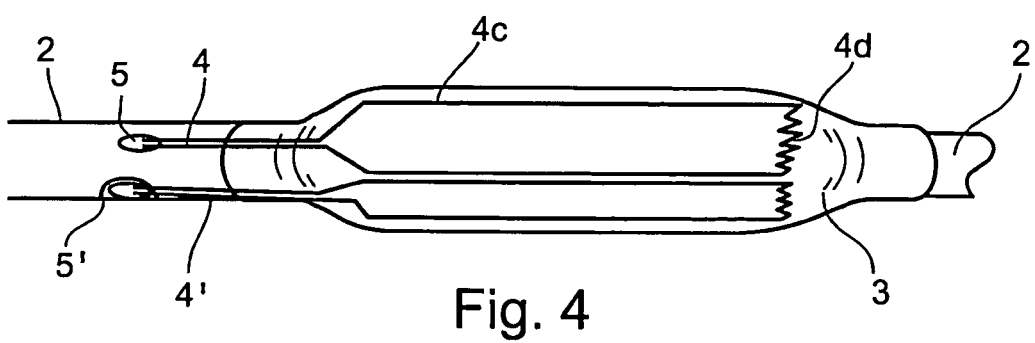

In the foregoing arrangements, the distal end of each of scraper cord is preferably fixed to the outer surface of the balloon. FIG. 4 illustrates another construction also including a plurality of scraper cords, but wherein both ends 4a, 4b of each cord, together with the folded intermediate portions 4c, are releasably retained on the outer surface of the balloon so as to permit complete removal of each scraper cord. The folded intermediate portion 4c of each scraper cord 4 illustrated in FIG. 4 further includes a circumferentially-extending section 4d of a direction-reversing or zigzag configuration, to accommodate the expansion of the balloon when radially expanded within the blood vessel before the scraping operation is started by the withdrawal of the cords as described above.

FIGS. 5a-5e illustrate various stages involved in using a scraper balloon catheter, as described above, for scraping away atheroma from the inner surface of a blood vessel. For purposes of example only, the illustrated catheter includes two scraper cords 4, 4', each of the folded, longitudinally-extending configuration shown in FIGS. 1a-1c.

Figure 5A:
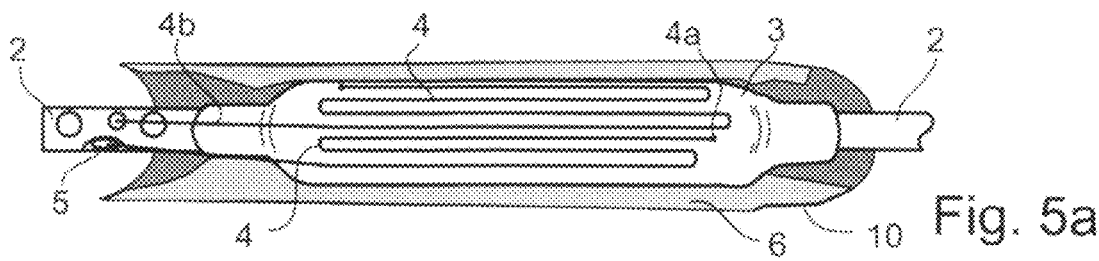
FIGS. 5a-5e illustrate different stages in the use of the catheter of FIGS. 1a-1c for removing atheroma in a blood vessel.
Figure 5B:
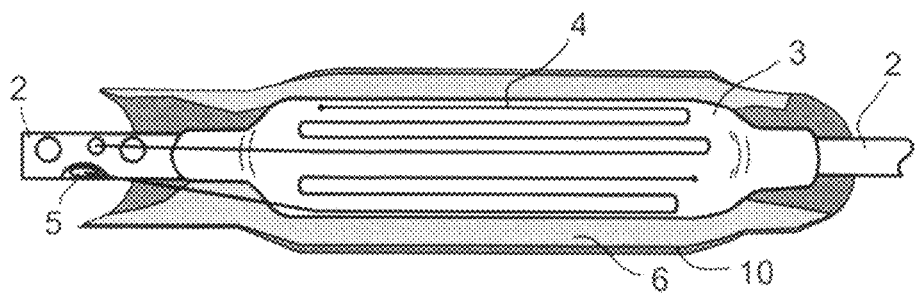
Figure 5C:
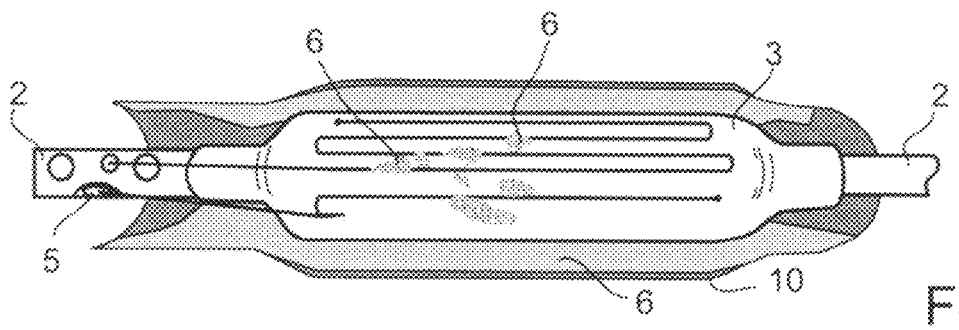
Figure 5D:
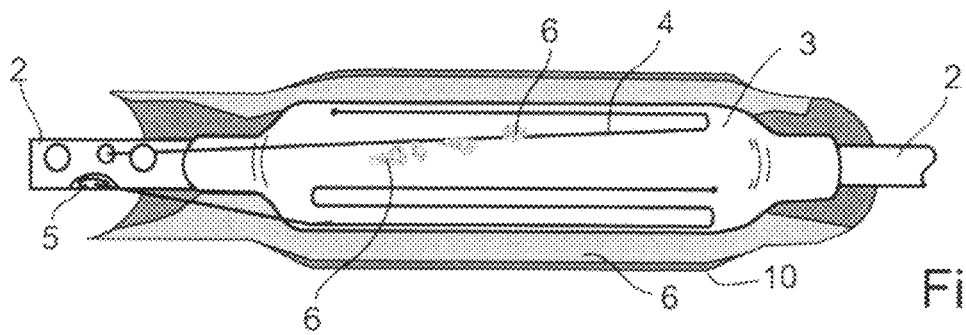

FIG. 5a illustrates the condition of the catheter in its initial non-inflated condition, after it has been manipulated within the blood vessel 10 to the location of the atheroma 6 to be removed; FIG. 5b illustrates the condition of the catheter after the balloon 3 has been inflated to bring its outer surface, as well as the scraper cords 4, 4' (FIGS. 2a, 3), into firm contact with the atheroma 6 on the inner surface of the blood vessel 10; FIG. 5c illustrates the condition wherein one scraper cord 4 has started to be moved through its respective opening 5 in the catheter tube 2 to cause the intermediate portion 4c of the cord to move along the outer surface of balloon 3, and thereby to scrape away some of the atheroma 6 engaged by the cord; and FIG. 5d illustrates the condition wherein the scraping operation is substantially coupled with respect to one scraper cord. It will be appreciated that the foregoing operations are repeated with respect to the other scraper cord 4, as well as any further scraper cords that may have been provided on the balloon.

Figure 5E:
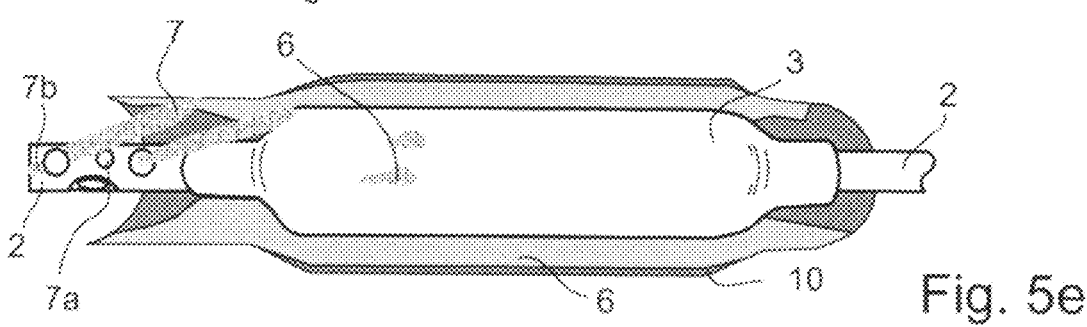

The so-removed atheroma may be collected in a "basket-type" collector. Preferably, however, a flushing fluid is applied under pressure between the outer surface of balloon 3 and inner surface of the blood vessel 10. This may be done before, during, and/or after the above-described scraping operation, to flush out the atheroma scraped away by the scraper cords. Such a flushing operation is illustrated in FIG. 5e, wherein flushing fluid 7 is applied under positive pressure to the space between the balloon and the blood vessel via opening 7a in the catheter tube 2, and is drawn out under negative pressure via opening 7b in the catheter tube.

Figure 6:
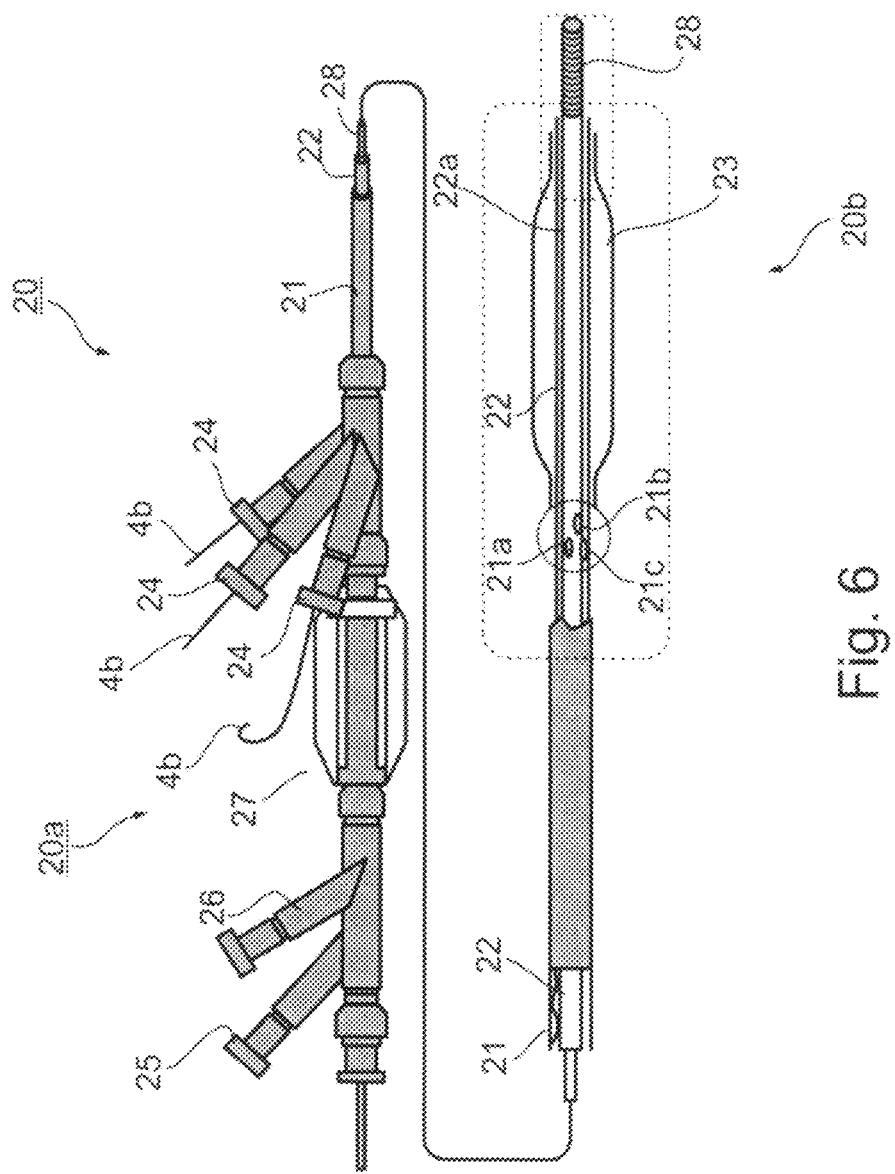
FIG. 6 illustrates both the proximal section and the distal section of a scraper balloon catheter (SBC) constructed in accordance with the present invention.

FIG. 6 illustrates a complete scraper balloon catheter (SBC) constructed in accordance with the invention. The illustrated catheter, generally designated 20, includes a proximal section 20a containing the various devices externally of the patient's body to be manipulated by the physician, and a distal section 20b connected to the proximal section 20a by inner and outer tubes 21, 22. Distal section 20b includes the balloon 23 to be introduced with the scraper cords 4 into the patient's blood vessel and manipulated to the site of the atheroma to be removed. The scraper cords may be of any of the foregoing configurations. They are releasably retained on the outer surface of the balloon 3, as described above, with their proximal ends 4b extending through Y-fittings 24 (one for each cord) in the proximal section 20a of the catheter.

Proximal section 20a of the catheter illustrated in FIG. 6 further includes another Y-fitting 25 for introducing the inflation fluid for inflating the balloon 23, and a further Y-fitting 26 for introducing the flushing fluid for flushing the atheroma scraped away from the blood vessel by the scraper cords 4, as described above with respect to FIG. 6e. The two Y-fittings 25, 26 are coupled to the Y-fittings 24 for the scraper cords by a clamshell device 27. The inner catheter tube 21 is formed at the distal section 20b with the openings 21a-21c for the scraper cords 4 passing through Y-fittings 24 and for the flushing fluid introduced via Y-fitting 26 in the proximal section. The outer catheter tube 22 is formed with an opening 22a communicating with the interior of balloon 23 for inflating the balloon by the inflation fluid introduced via Y-fitting 25.

FIG. 6 also illustrates the conventional guide wire 28 passing through the inner catheter tube 21 for guiding the manipulation of the balloon 23 in the distal section 20b to the treatment site of the blood vessel.

FIG. 7 illustrates a preferred construction of the distal section 20b of the catheter 20 illustrated in FIG. 6, and FIGS. 8a and 8b are transverse sectional views along lines a-a and b-b, respectively, of FIG. 7. As shown in these figures, the distal section 20b of the catheter is divided by four partitions 31-34 between the inner tube 21 and the outer tube 22 into four passageways 41-44, respectively. Passageways 41 and 43 are used for receiving the proximal ends of the scraper cords 4 as shown in FIG. 8a, and the remaining two passageways 42 and 44 are used for conducting the flushing fluid 7 to the space between the outer surface of balloon 23 and the inner surface of the blood vessel as shown in FIG. 8b. The deposits scraped away by scraper cords 4 are flushed into compartments 41 and 43 for removal from the catheter assembly. Thus, the outer catheter tube 22 is formed with an opening 44a (FIG. 8b) for establishing communication with the space between the outer surface of balloon 23 and the inner surface of the blood vessel, and with openings 41a and 43a (FIG. 8a) for establishing communication between the foregoing space and passageways 41 and 43 of the catheter assembly.

While the invention has been described with respect to several preferred embodiments, it will be appreciated that these are set forth merely for purposes of example, and that many other variations, modifications and applications of the invention may be made. For example, the illustrated catheter may be used for scraping the inner surfaces of other body channels. The described apparatus and method may also be used for removing deposits on the surfaces of other tubular structures, such as on the inner surface of pipes or other tubes.

Many other variations, modifications and applications of the invention will be apparent.

What is claimed is:

1. An apparatus for removing deposits from a selected location on an inner surface of a tubular structure, comprising:
    an expansible device constructed such than, in its non-expanded condition, it is introducible into the tubular structure, manipulatable therein to said selected location of the tubular structure, and radially-expansible therein to engage the inner surface of the tubular structure and the deposits to be removed; and
    at least one elongated scraper cord carried on an outer surface of said expansible device, said scraper cord being of a flexibility and a thickness to engage the inner surface of said tubular structure upon the expansion of said expansible device, and having a circumferentially-extending intermediate length axially movable with respect to and along the outer surface of said expansible device in its expanded condition to scrape away said deposits from the inner surface of the tubular structure,
    wherein said intermediate length of the scraper cord includes a plurality of interconnected direction-alternating sections such as to occupy a substantial portion of the outer surface of said expansible device,
    and wherein said scraper cord has a proximal end which, together with said intermediate length, is releasably retained on the outer surface of the expansible device such that, in the expanded condition of the expansible device, the proximal end of the scraper cord may be moved in the proximal direction to cause said intermediate length of the scraper cord to move between said outer surface of the expansible device and said inner surface of the tubular structure to thereby scrape away said deposits from said inner surface.

2. The apparatus according to claim 1, wherein said scraper cord has a distal end which is fixed to said expansible device.

3. The apparatus according to claim 1, wherein each of said plurality of interconnected direction-alternating sections extends longitudinally of the expansible device.

4. The apparatus according to claim 1, wherein each of said plurality of interconnected direction-alternating sections extends circumferentially of the expansible device.

5. The apparatus according to claim 1, wherein said apparatus further comprises a flushing device for applying a flushing fluid between the outer surface of said expansible device and the inner surface of said tubular structure to flush out the deposits scraped away from the inner surface of the tubular structure by said scraper cord.

6. The apparatus according to claim 1, wherein said expansible device is an inflatable balloon.

7. The apparatus according to claim 1, wherein said expansible device is configured and dimensioned for introduction into a blood vessel for removing atheroma or other substances deposited or accumulated thereon.

8. An apparatus for removing deposits from a selected location on an inner surface of a tubular structure, comprising:
    an expansible device constructed such that, in its non-expanded condition, it is introducible into the tubular structure, manipulatable therein to said selected location of the tubular structure, and radially-expansible therein to engage the inner surface of the tubular structure and the deposits to be removed; and
    at least one elongated scraper cord carried on an outer surface of said expansible device, said scraper cord being of a flexibility and a thickness to engage the inner surface of said tubular structure upon the expansion of said expansible device, and having a circumferentially-extending intermediate length axially movable with respect to and along the outer surface of said expansible device in its expanded condition to scrape away said deposits from the inner surface of the tubular structure,
    wherein said intermediate length of the scraper cord includes a plurality of interconnected direction-alternating sections such as to occupy a substantial portion of the outer surface of said expansible device,
    and wherein there are a plurality of said scraper cords carried on the outer surface of said expansible device and occupying different portions thereof.

9. An apparatus for removing deposits from a selected location on an inner surface of a tubular structure, comprising:
    an expansible device constructed such that, in its non-expanded condition, it is introducible into the tubular structure, manipulatable therein to said selected location of the tubular structure, and radially-expansible therein to engage the inner surface of the tubular structure and the deposits to be removed; and
    at least one elongated scraper cord carried on an outer surface of said expansible device, said scraper cord being of a flexibility and a thickness to engage the inner surface of said tubular structure upon the expansion of said expansible device, and having a circumferentially-extending intermediate length axially movable with respect to and along the outer surface of said expansible device in its expanded condition to scrape away said deposits from the inner surface of the tubular structure, wherein said intermediate length of the scraper cord includes a plurality of interconnected direction-alternating sections such as to occupy a substantial portion of the outer surface of said expansible device, and wherein there are a plurality of said scraper cords carried on the outer surface of said expansible device and occupying different layers thereon.

10. An apparatus for removing deposits from a selected location on an inner surface of a tubular structure, comprising:

an expansible device constructed such that, in its non-expanded condition, said expansible device is introducible into the tubular structure, manipulatable therein to said selected location of the tubular structure, and radially-expansible therein to engage the inner surface of the tubular structure and the deposits to be removed; and a scraper cord arrangement including at least one scraper cord carried on an outer surface of said expansible device, said at least one scraper cord being of a flexibility and a thickness to engage the inner surface of said tubular structure upon the expansion of said expansible device, and having a circumferentially-extending intermediate length axially movable with respect to and along the outer surface of said expansible device in its expanded condition to scrape away said deposits from the inner surface of the tubular structure, wherein said scraper cord arrangement is deployed in a pattern on the outer surface of the expansible device such that said pattern spans a majority of a circumference of the surface of the expansible device.

11. The apparatus according to claim 10, wherein a part of said at least one scraper cord is releasably retained on the outer surface of the expansible device such that, in the expanded condition of the expansible device, tension applied to a proximal region of said scraper cord progressively releases the scraper cord from the outer surface of the expansible device and displaces said scraper cord so as to move between said outer surface of the expansible device and the inner surface of the tubular structure for scraping away the deposits from the inner surface.

12. The apparatus according to claim 11, wherein a deployment of said at least one scraper cord on the outer surface of the expansible device is such that, when the expansible device is in the expanded condition and the proximal region of said scraper cord is drawn in an axial direction, a resulting displacement of at least a part of said scraper cord includes a component of motion in a circumferential direction.

13. The apparatus according to claim 10, wherein a part of said at least one scraper cord includes a plurality of interconnected direction-alternating sections.

14. The apparatus according to claim 13, wherein each of said plurality of interconnected direction-alternating sections extends longitudinally along the expansible device.

15. The apparatus according to claim 13, wherein each of said plurality of interconnected direction-alternating sections extends circumferentially around the expansible device.

16. The apparatus according to claim 10, wherein said scraper cord arrangement comprises a plurality of said scraper cords deployed on distinct regions of the outer surface of said expansible device.

17. The apparatus according to claim 10, wherein said scraper cord arrangement comprises a plurality of said scraper cords deployed in overlapping layers on the outer surface of said expansible device.

18. The apparatus according to claim 10, further comprising a flushing device for applying a flushing fluid between the outer surface of said expansible device and the inner surface of said tubular structure to flush out the deposits scraped away from the inner surface of the tubular structure by said scraper cord.

19. The apparatus according to claim 10, wherein said expansible device is an inflatable balloon.

20. The apparatus according to claim 10, wherein said expansible device is configured and dimensioned for introduction into a blood vessel for removing atheroma or other substances deposited or accumulated thereon.

* * * * *